(12) United States Patent
Pieper et al.

(10) Patent No.: US 8,329,975 B2
(45) Date of Patent: Dec. 11, 2012

(54) ELIMINATION OF RESIDUAL TRANSFER LINE RAFFINATE FROM FEED TO INCREASE NORMAL PARAFFIN SEPARATION UNIT CAPACITY

(75) Inventors: Jeffrey L. Pieper, Des Plaines, IL (US); Stephen W. Sohn, Arlington Heights, IL (US); Peter M. Bernard, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 182 days.

(21) Appl. No.: 12/972,953

(22) Filed: Dec. 20, 2010

(65) Prior Publication Data

US 2012/0152802 A1     Jun. 21, 2012

(51) Int. Cl.
*C07C 7/12*     (2006.01)
(52) U.S. Cl. ......................................... 585/820; 585/822
(58) Field of Classification Search .................... None
See application file for complete search history.

(56) References Cited

U.S. PATENT DOCUMENTS

| | | | |
|---|---|---|---|
| 4,006,197 A | 2/1977 | Bieser | |
| 4,118,429 A | 10/1978 | Fritsch et al. | |
| 5,912,395 A | 6/1999 | Noe | |
| 7,208,651 B2* | 4/2007 | Frey | 585/828 |
| 2005/0269268 A1* | 12/2005 | Hotier | 210/659 |
| 2006/0199989 A1 | 9/2006 | Frey | |
| 2008/0237132 A1* | 10/2008 | Hotier et al. | 210/659 |
| 2009/0050221 A1* | 2/2009 | Baird | 137/625.46 |
| 2011/0315634 A1* | 12/2011 | Hotier et al. | 210/659 |
| 2012/0157744 A1* | 6/2012 | Pieper et al. | 585/822 |

OTHER PUBLICATIONS

U.S. Appl. No. 13/324,013, filed Dec. 13, 2011; Pieper et al.

* cited by examiner

*Primary Examiner* — Tam M Nguyen
(74) *Attorney, Agent, or Firm* — Arthur E Gooding

(57) ABSTRACT

A process to increase the capacity of the adsorbent in a normal paraffin adsorption separation system is presented. A tertiary flush stream is used to improve the capacity of the simulated moving bed system by flushing residual raffinate from the feed transfer line. The flushing removes residual raffinate containing desorbent that competes with the adsorption of normal paraffins from the feedstream. The flush stream is a material that will displace fluid in the column, but will not enter the pores of the adsorbent.

20 Claims, 2 Drawing Sheets

US 8,329,975 B2

ELIMINATION OF RESIDUAL TRANSFER LINE RAFFINATE FROM FEED TO INCREASE NORMAL PARAFFIN SEPARATION UNIT CAPACITY

FIELD OF THE INVENTION

The field of the invention relates to adsorption separation processes. In particular, the invention relates to the continuous simulated moving bed adsorption separation process for the separation of hydrocarbons.

BACKGROUND OF THE INVENTION

The separation of close boiling point components, or the separation of organic isomers is important for a variety of petrochemical processes. The use of adsorption separation processes has enabled the normally very difficult separation of components in a mixture. The adsorption separation process for a large scale process uses the simulated moving bed design for a continuous separation of components in the mixture. The simulated moving bed process is described in U.S. Pat. No. 2,985,589 by Broughton et al. The simulated moving bed process uses a simulated countercurrent movement of the adsorbent with the fluid mixture to be separated.

The process is performed using established commercial technology wherein the adsorbent is placed in a plurality of adsorbent beds and between each pair of adsorbent beds are access ports for admitting and withdrawing fluid from the system. As the process progresses, the streams involved in the process are shifted from one adsorbent bed to the next adjacent adsorbent bed. Normally, there are four streams, a feedstream comprising the mixture to be separated, an extract stream comprising the preferentially adsorbed component, a desorbent stream for displacing the adsorbed component, and a raffinate stream comprising the remaining components of the feedstream mixture. Each stream is shifted simultaneously and in the same direction along the adsorbent beds. With each shift in location, fluid is delivered or removed from a different bed. With this progression, the preferentially adsorbed component is separated from the mixture.

Many aspects of the adsorption separation process must be considered. For a given separation, the process can be a molecular sieving process, or in other cases, the process can be a separation due to electrostatic forces. The general process relies on the differential adsorption of the different components in the mixture. One, or more, component(s) is preferentially adsorbed, and the remaining components are swept along as the fluid continues to flow over the adsorbent. A particular separation also needs to consider the type of adsorbent material used, and operating conditions, as well as appropriate desorbents that can be used.

Adsorption separation uses expensive equipment, and the equipment is not readily replaced to increase the production of a product stream. With increasing demand for the products from adsorption separation processes, increasing the throughput, capacity and recovery of the products is desirable without having to replace the equipment.

SUMMARY OF THE INVENTION

This invention is an improvement to the adsorption separation process that utilizes a simulated moving bed process. The simulated moving bed system comprises a multiport adsorption column where the ports are sequentially used to admit and withdraw fluid streams. The process is for the separation of selected components from a hydrocarbon mixture, where the selected components are preferentially adsorbed onto the adsorbent while the remaining components are swept out of the adsorption column. The process includes passing a feedstream comprising the hydrocarbon mixture to a first port in the adsorption column. A desorbent stream is passed to a second port in the adsorption column, and an extract stream is withdrawn from a third port comprising the preferentially selected components. A raffinate stream is withdrawn from a fourth port comprising the non-adsorbed components from the feedstream. An inefficiency results in the simulated moving bed system from the fact that the transfer line used to withdraw the raffinate stream from the fourth port is used sequentially to admit the feedstream into the first port. The process further includes passing a tertiary flush stream through a fifth port downstream relative to the first port, and withdrawing material from inside the adsorption column to displace raffinate material inside the transfer line. The raffinate material flushed from the transfer line is combined with the raffinate stream being withdrawn from the adsorption column. The tertiary flush stream has a lower amount of desorbent compared to the raffinate material and increases the capacity of the adsorbent for the separation process.

In a second embodiment, the invention is similar to the first embodiment, except for the position of the fifth port and the tertiary flush stream comprises a fractionated desorbent material which does not enter the adsorbent pores. The fifth port is upstream relative to the second port, or the raffinate withdrawal. The tertiary flush stream clears the transfer line of raffinate material after the raffinate withdrawal port has been moved to a neighboring port, and the material is pushed away from the column. The withdrawal of the flush stream can be included in an increase in the withdrawal of the raffinate stream. The flush stream contains no desorbent material which can enter the adsorbent selective pores to increase the capacity of the adsorbent for the separation process even further than the first embodiment.

Other objects, advantages and applications of the present invention will become apparent to those skilled in the art from the following detailed description and drawings.

DETAILED DESCRIPTION OF THE INVENTION

Figure 1:
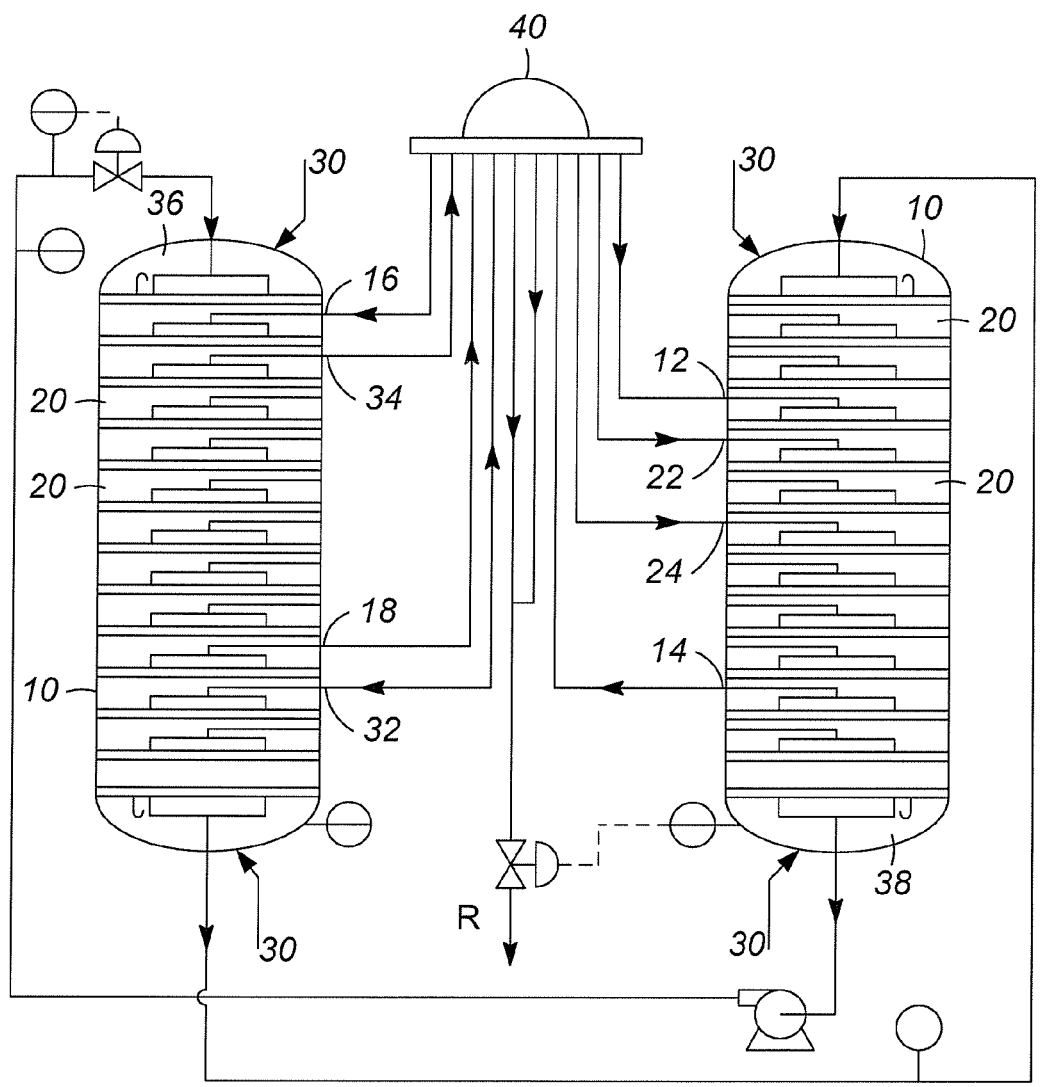
FIG. 1 is a first embodiment of the invention showing the process.

The use of adsorption separation technologies for product purification include many areas in hydrocarbon processing. The adsorption separation process is based on the simulated moving bed technology, as presented in Broughton et al., in U.S. Pat. No. 2,985,589 and is incorporated by reference in its entirety. The process relies upon creating different zones within the adsorption beds. There is an adsorption zone wherein the preferentially adsorbed component is removed from the feedstream as the feedstream passes through the adsorption beds. There is also a desorption zone wherein a desorbent is passed through the adsorbent beds to displace the preferentially adsorbed component from the feedstream. The adsorption zone and desorption zones are separated by buffer zones to enable a significant enrichment of the preferentially adsorbed component.

The preferentially adsorbed component is removed in an extract stream with the desorbent, where the mixture of desorbent and preferentially adsorbed component are separated in a distillation column. The choice of desorbent is selected to have a substantially different boiling point from the adsorbed component which enables a relatively cheap separation by distillation. The feedstream with the adsorbed component removed is withdrawn in a raffinate stream. The raffinate stream is processed to recover desorbents that have been carried out with the raffinate stream and to recycle any desorbents. Adsorption capacity and purity are important aspects for increasing the throughput of higher purity products without increasing the size of existing adsorption separation systems.

For purposes of this invention, the terms upstream and downstream when used in reference to the movement of incrementing of the ports for the transfer line connections in a simulated moving bed design, upstream refers to the direction that the port has already been, and downstream refers to the direction the port is being moved.

The present invention improves the adsorption capacity of the adsorption beds, or adsorption zones, in an adsorption separation system. This is also known as a simulated moving bed system, wherein the adsorption separation simulates the counter-current contact of a feedstream with an adsorbent. In a simulated context, the fluid flows down a column of beds, and the solid adsorbent moves up the column of beds through 4 zones in the process. In actuality, the zones move down the column, as the different streams are added or withdrawn from the column, and the positions of the streams entering and leaving the column also move to coincide with the shifting of the zones. Each adsorption zone, or individual adsorbent bed, has a fluid inlet and a fluid outlet, and the adsorption zones are serially connected through fluid connections.

The process has an adsorption zone, or Zone I, of the chamber where the feedstream contacts the adsorbent and selectively adsorbs the desired components. This removes the selected components from the flowing liquid, which becomes the raffinate stream. The raffinate stream is removed from the bottom of Zone I where the desired components have been adsorbed onto the adsorbent leaving the undesired components in the raffinate stream. As the process is a continuous process, the raffinate stream also includes any residual desorbent left in the column as the process stream flows through the column.

After the adsorption zone beds have passed through the purification zone, a liquid desorbent is added to the desorbent zone, or Zone III, where the desorbent displaces the selected component that has been adsorbed on the adsorbent. Zone III is separated from Zone I by the purification Zone II. The stream comprising the desorbent and the selected component makes up the extract stream which is removed from the column. The desorbent is selected to readily displace the selected component, but is also selected to be readily separated from the selected component in a distillation process.

Zone I and Zone III are also separated by a buffer Zone IV, to prevent the contamination of liquid from Zone III with the liquid from Zone I. More information on the process is available in numerous patents and references, including U.S. Pat. No. 5,912,395, which is incorporated by reference in its entirety.

In some adsorption processes, the adsorption is through physical sieving, wherein the pores are sized to allow molecules that will fit within the pores. In one process, the separation of normal paraffins from a mixture uses small pored adsorbents and permits only normal paraffins into the pores for adsorption. The present invention aims to increase the capacity of the adsorbent for the selected hydrocarbon, through the displacement of desorbent which occupies the pores included with the raffinate stream in the transfer line with a tertiary flush stream after the raffinate stream containing desorbent is otherwise flushed through the transfer line into the adsorbent bed by the feedstream. The desorbent from the transfer line enters the pores during the adsorption step, and is in competition with the selected hydrocarbon for the pore space. By displacing some or all of the desorbent before the feedstream enters the adsorbent beds, the capacity of the adsorbent beds is increased.

The present invention, as shown in FIG. 1, includes passing a feedstream comprising a mixture of hydrocarbons, and in particular paraffins, to an adsorbent zone 20 through a first port 22, in an adsorption column 10. For convenience of the description and drawing, the adsorption column is shown as two columns 10, and can be a single or multiple columns, but the usual practice is for two columns containing the adsorbent beds. In this figure, the fluid from the bottom bed of the left hand column can be transferred by pressure or pumped to the top of the right hand column and the fluid from the bottom bed of the right hand column is pumped to the top of the left hand column, making for a continuous string of adsorbent beds. The usual practice for transferring fluid from the bottom bed of the left hand column to the top of the right hand column is transfer by pressure. The number of adsorbent beds is at least 8 with a preferred number of at least 20 and a more preferred number of at least 24 adsorbent beds. The number of adsorbent beds will depend upon the desired purity and recovery of normal paraffins, and can be 12 adsorbent beds for some processes. It is preferred that Zones I, II and III have at least 6 beds each. The normal paraffins in the mixture are preferentially adsorbed by the adsorbent and the non-normal paraffins remain in the liquid phase. The non-normal paraffins are in the raffinate stream, which is withdrawn from the adsorption column 10 through a second port 14. As the process progresses, a desorbent stream is passed through a third port 16 to displace the adsorbed normal hydrocarbon. The displaced normal hydrocarbon with the desorbent creates an extract stream which is withdrawn through a fourth port 18. The system further includes an inlet line flush 12.

The process further includes the addition of a tertiary flush stream through a fifth port 24, and the withdrawal of the tertiary flush stream is through an extra channel in the rotary valve 40 and is combined with the raffinate stream leaving the rotary valve 40 for an increase in the raffinate stream. The fifth port 24 is preferably one or two ports downstream of the first port 22, or the feedstream inlet port. The tertiary flush stream displaces desorbent included with the raffinate stream in the transfer line which would otherwise be flushed into the adsorption column 10 by the feedstream, thereby opening up more of the pores for the desired normal hydrocarbon to be adsorbed. The tertiary flush stream for this example will contain a lower concentration of desorbent compared to the raffinate stream. This invention is obtained through a modification of the rotary valve 40. The tertiary flush stream uses an extra channel in the rotary valve 40 for adding a tertiary flush net process stream line from the rotary valve 40 to the raffinate net process stream line. An alternate embodiment to the extra channel in the rotary valve 40 is for an additional line tertiary flush stream line added to each of the individual transfer lines near the end by the rotary valve 40 and connecting the other end of each of the tertiary flush stream lines to the raffinate net process stream withdrawn from the rotary valve 40. These modifications to the rotary valve 40 or the additional lines are applicable to all embodiments.

The process will also include a fractionated desorbent stream which is used for zone flush 32 and the line flush in 12. The zone flush 32, which through regulation of the flow, flushes the undesired feed components down through the purification Zone II and away from the desorption Zone III while at the same time preventing loss of desorbed normal paraffins from the desorption Zone III, through the purification Zone II and into the adsorption Zone I. This facilitates maintaining the purity of the extract during the desorption step. The line flush in port 12 is upstream of the feed port 22 and removed feedstream material from the transfer line to prevent contamination of the extract with feed resulting in lower purity. The line flush out port 34 is downstream of the desorbent port 16 and flushes the extract stream in the transfer line to the extract column for improved normal paraffin recovery.

For the separation of C10 to C14 normal paraffins, a typical desorbent is n-pentane mixed with other hydrocarbons such as isooctane or a mixture of isooctane and an aromatic component such as paraxylene. The desorbent is typically fractionated to remove the n-pentane leaving a preferred flush stream comprising isooctane or a mixture of isooctane and paraxylene. For such a system, a preferred tertiary flush stream is the same as the flush stream comprising isooctane or a mixture of isooctane and paraxylene.

For this example, the tertiary flush stream is withdrawn from the adsorption column 10 in an amount between 50% and 300% of the volume of the longest transfer line between the rotary valve 40 and the column 10, or preferably the amount is between 100% and 200%. A more preferred amount for the tertiary flush stream is between 80% and 120% of the volume of the longest transfer line between the rotary valve 40 and the column 10. The amount of tertiary flush stream should clear the transfer line so as to displace desorbent but should not be too excessive to result in losses of paraffins from the adsorption column 10 to the raffinate stream.

The transfer lines before the feedstream transfer line contain raffinate material. The raffinate can have desorbent material containing 20% to 30% n-pentane. The tertiary flush stream from the adsorption column 10 will contain between 5% and 15% n-pentane. The n-pentane portion of the desorbent competes with the normal paraffins in the feedstream for the space in the pores of the adsorbent. By removing at least a portion of the n-pentane portion of the desorbent in the transfer line by replacing the residual raffinate with the tertiary flush stream, the capacity of the adsorbent is increased. This increase in capacity is obtained through modification of the rotary valve and external piping tie-ins for the tertiary flush stream, resulting in a rapid payback for an existing adsorption separation system.

In one embodiment of the invention, the process is for the recovery of normal paraffins from a hydrocarbon mixture where the normal paraffins have from 6 to 30 carbon atoms, with a preferred range between 6 and 20 carbon atoms. The selection of desorbent will depend upon the range of normal paraffins to be recovered in the process. The desorbent will comprise a normal paraffin having a different boiling point than the boiling point of the selectively adsorbed normal paraffins separated from the feedstream. For selected adsorbed normal paraffins in the C10 to C13 range, a desorbent can be n-pentane, or a mixture of n-pentane and a relatively light hydrocarbon such as isooctane. For heavier selectively adsorbed normal paraffins, such as in the C10 to C20 range, n-hexane or a mixture of n-hexane and isooctane can be used for the desorbent.

When the process is for the recovery of light n-paraffins, such as in the C6 to C10 range, the desorbent used would comprise a heavier normal paraffin. One example of a heavier normal paraffin is n-C12.

Figure 2:
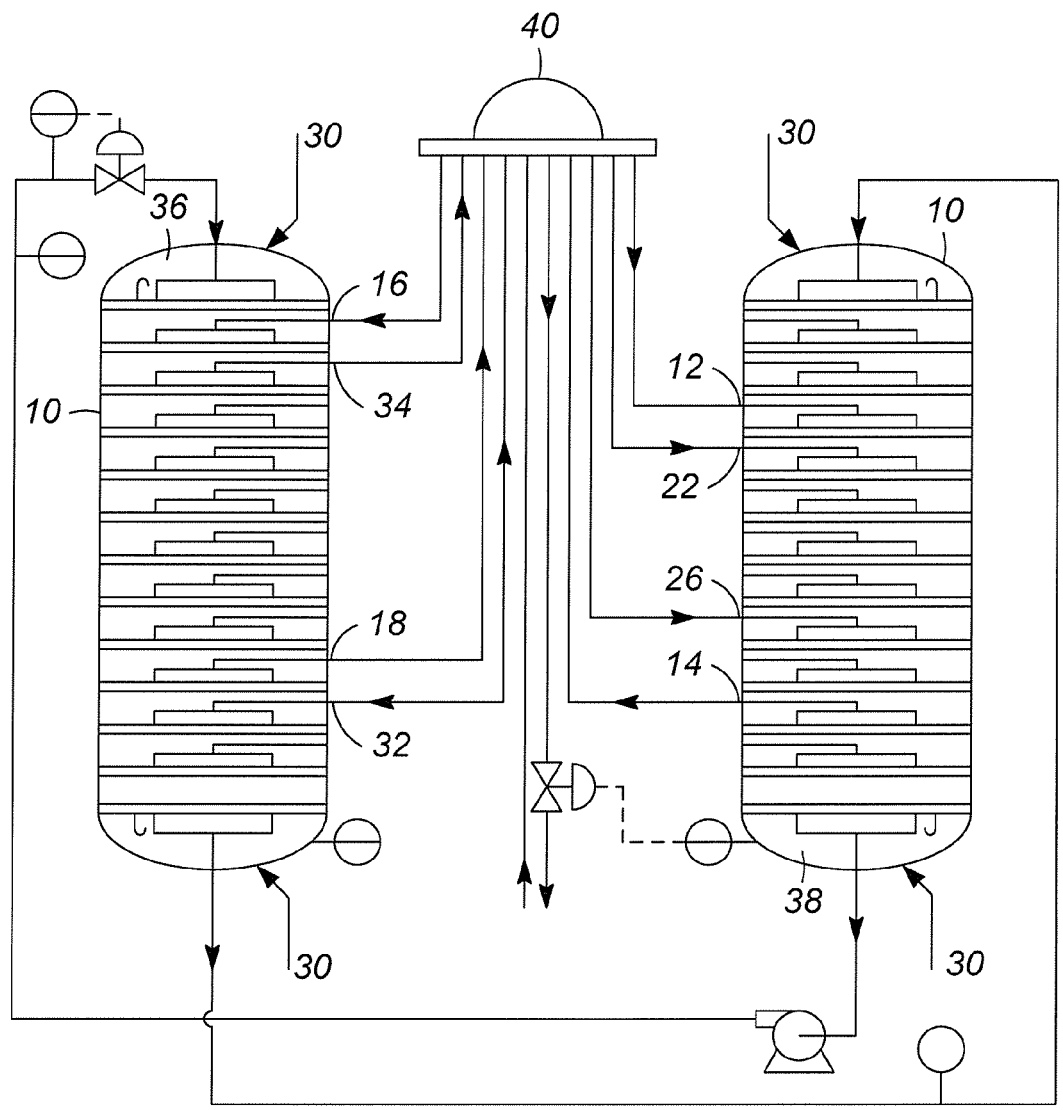
FIG. 2 is a second embodiment of the invention.

In a second embodiment as shown in FIG. 2, the process uses the same material as the flush stream used for the zone flush and the line flush in stream for the tertiary flush stream, and passes the tertiary flush stream in through a different location. The tertiary flush stream is used to displace the desorbent and raffinate material in the transfer line, but can reduce the amount of residual n-pentane by a greater amount since the flush is a fractionated desorbent material containing no n-pentane. This method can increase capacity even further than the first embodiment, but will require higher volumes of flush material.

The process includes passing a feedstream comprising a mixture of normal and non-normal paraffins through a first port 22 to an adsorbent bed where the normal paraffins are selectively adsorbed. The non-normal paraffins preferentially remain in the fluid phase and form a raffinate stream. The raffinate stream is withdrawn from a second port 14. A desorbent is passed into the column through a third port 16 and displaces the normal paraffin that has been adsorbed onto the adsorbent. The displaced normal paraffin with some desorbent forms an extract stream which is withdrawn from a fourth port 18.

The process further includes passing a tertiary flush stream to the column through a fifth port 26 wherein the fifth port 26 is positioned upstream of the raffinate withdrawal port, or second port 14. Preferably, the tertiary flush stream is passed into the column one or two ports upstream of the second port 14. The tertiary flush stream is comprised of a material that will not occupy the pores of the adsorbent. In the second embodiment, a preferred tertiary flush material is isooctane or a mixture of isooctane and paraxylene.

The flush stream in the second embodiment, also flushes out the raffinate from the lines through which it passes. The flush stream in the second embodiment is in an amount between 50% and 300% of the volume of the longest transfer line between the rotary valve and the column. Preferably the amount is between 100% and 200% of the volume of the longest transfer line between the rotary valve and the column.

The process can further include a top and bottom head flush 30. The column has an upper head region 36 above the top bed, and a lower head region 38 below the bottom bed. The head regions are flushed with a flush stream to prevent cross contamination of adsorptive column zones across the heads as the process cycles through the column. The flush stream can comprise the same material used in the tertiary flush, and is selected for the ability to separate the flush stream components from either the raffinate material, or the extract material. Preferably the flush stream is a material that will not occupy the pores in the adsorbent. A preferred flush material for the process of recovering normal paraffins in the C10 to C13 range is isooctane. The flush material is passed into the adsorption column 10, pushing the residual raffinate into the column 10 and increasing the withdrawal of raffinate from the adsorption column 10. This removes a significant portion or all of the n-pentane portion of the desorbent from the transfer line by replacing the residual raffinate with the tertiary flush stream and increases the bed capacity.

The first embodiment, in addition to displacing desorbent from the adsorbent pores, reduces the amount of desorbent separated from the raffinate stream. The raffinate stream is passed to a separation unit to recover desorbent and other materials from the raffinate stream. The usual separation unit is a distillation column where the boiling point of the desorbent and flush stream material is different from the raffinate components and readily separated and recycled for use in the adsorption separation system.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for increasing the yields of normal paraffins in an adsorption separation system, comprising:
passing a feedstream comprising a mixture of paraffins through a first port, wherein the normal paraffins in the mixture are preferentially adsorbed by the adsorbent and where the non-normal paraffins remain in the fluid phase, and where the adsorbent is divided into a plurality of adsorbent bed zones that are serially connected through fluid connections, and where each adsorbent bed has a fluid inlet and a fluid outlet;
withdrawing a raffinate stream comprising non-normal paraffins through a second port;
passing a desorbent stream comprising a desorbent through a third port;
withdrawing an extract stream comprising normal paraffins through a fourth port;
passing a tertiary flush stream through a fifth port; and
withdrawing the tertiary flush stream through a sixth port;
wherein each of the streams are passed through different transfer lines in fluid communication with the ports and are directed through a channel in a rotary valve.

2. The process of claim 1 wherein the fifth port is in a downstream position relative to the feedstream.

3. The process of claim 2 wherein the fifth port is one or two ports downstream of the feedstream port.

4. The process of claim 1 wherein the inlet flush stream comprises a flush material that will not occupy the pores in the adsorbent.

5. The process of claim 4 wherein the tertiary flush stream comprises Zone I materials, comprising feedstream components and desorbent materials.

6. The process of claim 1 wherein the tertiary flush stream is in an amount between 50% and 300% of the fluid sufficient to displace the fluid in the longest transfer line between the port and rotary valve channel.

7. The process of claim 6 wherein the tertiary flush stream is in an amount between 80% and 120% of the fluid sufficient to displace the fluid in the longest transfer line between the port and rotary valve channel.

8. The process of claim 1 wherein the number of adsorbent bed zones is at least 12.

9. The process of claim 1 wherein the feedstream comprises a mixture of hydrocarbons having 6 to 30 carbon atoms.

10. The process of claim 1 wherein the desorbent comprises a normal paraffin having a different boiling point than the boiling point of the normal paraffin separated from the feedstream.

11. A process for increasing the yields of normal paraffins in an adsorption separation system, comprising:
passing a feedstream comprising a mixture of paraffins through a first port, wherein the normal paraffins in the mixture are preferentially adsorbed by the adsorbent and where the non-normal paraffins remain in the fluid phase, and where the adsorbent is divided into a plurality of adsorbent bed zones that are serially connected through fluid connections, and where each adsorbent bed has a fluid inlet and a fluid outlet;
withdrawing a raffinate stream comprising non-normal paraffins through a second port;
passing a desorbent stream comprising a desorbent through a third port;
withdrawing an extract stream comprising normal paraffins through a fourth port; and
passing an tertiary flush stream through a fifth port, wherein the fifth port is positioned upstream relative to the second port;
wherein the first port is at the beginning of the adsorption zone, the second port is at the end of the adsorption zone, the third port is at the beginning of the desorption zone, and the fourth port is at the end of the desorption zone, and wherein the adsorption zone and desorption zone are separated by buffer zones.

12. The process of claim 11 wherein the fifth port is positioned one or two ports upstream of the second port.

13. The process of claim 11 wherein the tertiary flush stream is in an amount between 50% and 300% of the fluid sufficient to displace the fluid in the longest transfer line between the port and rotary valve channel.

14. The process of claim 13 wherein the tertiary flush stream is in an amount between 100% and 200% of the fluid sufficient to displace the fluid in the longest transfer line between the port and rotary valve channel.

15. The process of claim 11 further comprising:
an inlet zone flush stream for sweeping material out of a buffer zone;
an inlet line flush stream; and
an outlet line flush stream.

16. The process of claim 11 further comprising an upper head flush stream for flushing the head region above the first bed and a lower head flush stream for flushing the head region below the last bed.

17. The process of claim 11 wherein the tertiary flush stream comprises a flush material that will not occupy the pores in the adsorbent.

18. The process of claim 11 wherein the desorbent comprises a normal paraffin having a different boiling point than the boiling point of the normal paraffin separated from the feedstream.

19. The process of claim 18 wherein the desorbent comprises a mixture of n-pentane and isooctane.

20. The process of claim 18 wherein the desorbent comprises a mixture of n-pentane, isooctane and paraxylene.

* * * * *